United States Patent
McCaulley et al.

(10) Patent No.: US 6,803,032 B2
(45) Date of Patent: Oct. 12, 2004

(54) ASTRINGENT SHAVE PREPARATIONS

(75) Inventors: James A. McCaulley, Ringoes, NJ (US); Pat Hoontrakul, Bethlehem, PA (US)

(73) Assignee: Cognis Corporation, Cincinnati, OH (US)

( * ) Notice: Subject to any disclaimer, the term of this patent is extended or adjusted under 35 U.S.C. 154(b) by 88 days.

(21) Appl. No.: 10/008,663

(22) Filed: Nov. 7, 2001

(65) Prior Publication Data

US 2002/0141960 A1 Oct. 3, 2002

Related U.S. Application Data

(60) Provisional application No. 60/246,355, filed on Nov. 7, 2000.

(51) Int. Cl.⁷ .................................................. A61K 7/15
(52) U.S. Cl. ........................................ 424/73; 514/848
(58) Field of Search ............................................ 424/73

(56) References Cited

U.S. PATENT DOCUMENTS

| 4,933,177 A | * | 6/1990 | Grollier et al. | 424/74 |
| 4,944,939 A | * | 7/1990 | Moore | 424/73 |
| 4,963,350 A | * | 10/1990 | Goldstein et al. | 424/73 |
| 6,001,340 A | * | 12/1999 | Rosen et al. | 424/73 |
| 6,165,456 A | | 12/2000 | Barnet et al. | 424/73 |

FOREIGN PATENT DOCUMENTS

| JP | 63126812 A | * | 5/1988 | A61K/7/00 |
| JP | 11322534 A | * | 11/1999 | A61K/7/00 |
| JP | 411322534 A | * | 11/1999 | A61K/7/00 |
| JP | 2000191513 A | * | 7/2000 | A61K/7/50 |

* cited by examiner

*Primary Examiner*—James M. Spear
(74) *Attorney, Agent, or Firm*—Aaron R. Ettelman; Steven J. Trzaska

(57) ABSTRACT

A shaving composition containing a skin-tightening effective amount of an astringent additive, wherein the shaving composition is applied onto human skin prior to shaving.

12 Claims, No Drawings

ASTRINGENT SHAVE PREPARATIONS

CROSS-REFERENCE TO RELATED APPLICATIONS

This application claims the benefit of copending provisional application serial No. 60/246,355 filed on Nov. 7, 2000.

STATEMENT REGARDING FEDERALLY SPONSORED RESEARCH AND DEVELOPMENT

Not applicable.

BACKGROUND OF THE INVENTION

The present invention generally relates to shaving preparations which are applied onto a person's skin prior to shaving. A common problem associated with the act of shaving is the formation of razor bumps on the shaved surface, i.e., pseudofolliculitis barbae (PFB). This is a shaving-induced condition caused by re-entrant penetration of newly-cut hairs into the skin resulting in significant skin irritation.

Hairs which lie nearly parallel to the skin have a tendency of being cut at an acute angle, producing sharp points that can penetrate into the skin. Those individuals whose hair follicles have a strong natural curl are even more susceptible to this type of skin condition. The re-entrant hair induces an antigenic, foreign body reaction, leading to the formation of papules or cysts that appear as raised bumps on the skin's surface. These raised bumps are further irritated by subsequent acts of shaving. The local irritation may be further worsened by bacterial infection, as is oftentimes the case with acne.

Efforts have been made to prevent and/or inhibit PFB from occurring. These efforts, however, have focused on preventing the initial re-entrant penetration of newly shaved hairs using chemical compounds commonly employed in the treatment of acne such as, for example, benzoyl peroxide, acetylsalicylic acid, and the like.

BRIEF SUMMARY OF THE INVENTION

The present invention is directed to a shaving composition containing a skin-tightening effective amount of an astringent compound, wherein the shaving composition is applied onto human skin prior to shaving.

The present invention is also directed to a process for inhibiting re-entrant penetration of newly shaved hair into human skin involving:

(a) providing a shaving composition containing a skin-tightening effective amount of an astringent compound; and (b) applying the shaving composition onto human skin prior to shaving.

DETAILED DESCRIPTION OF THE INVENTION

Other than in the operating examples, or where otherwise indicated, all numbers expressing quantities of ingredients and/or reaction conditions, are to be understood as being modified in all instances by the term "about".

It has surprisingly been discovered that by applying a shaving composition containing an astringent compound onto human skin prior to shaving, the re-entrant penetration of newly shaved hairs back into the skin can be effectively inhibited. The shaving composition of the present invention also provides for a closer shave because the astringent contained in the shaving composition causes the skin to tighten, thereby enabling a much smoother shave. Moreover, application of this composition prior to shaving also causes the hair follicles to lie more upright, which also facilitates a closer shave and causes the shaved hairs to have blunt rather than sharp ends.

While any suitable astringent compound may be employed such as, for example, witch hazel extract or zinc paraphenolsulfonate, a particularly effective astringent additive is a mixture of butylene glycol and *Fomes Officinalis* (mushroom extract) commercially available from Laboratories Serobiologiques under the tradename LARICYL® LS 8865.

The astringent compound may be employed in any conventional type of shaving composition. A particularly preferred shaving composition is a shaving gel. This type of composition is typically in the form of an oil-in-water emulsion containing water and a water-soluble soap component and/or synthetic wetting agent.

The primary component of the shaving gel is water, preferably deionized or distilled water. The soap component is typically a water soluble salt of a fatty acid. Examples thereof include, but are not limited to, triethanolamine soaps of stearic and palmitic acids, animal-derived soaps, vegetable-derived soaps, and mixtures thereof. Synthetic wetting agents, when used, are typically of the nonionic variety. Examples thereof include, but are not limited to, water-soluble alkoxylated fatty alcohols, water soluble polyoxyethylene ethers of alkyl-substituted phenols, and the like.

The shaving gel may also include a self-foaming agent, if desired, which provides for the formation of foam when spread over a person's skin and beard. Typically, a low boiling aliphatic hydrocarbon is used as the volatile self-foaming agent. Examples thereof include, but are not limited to, n-pentane, isopentane, neopentane, n-butane, isobutane, and mixtures thereof.

According to one aspect of the present invention, there is provided a shaving composition containing an astringent additive for use prior to shaving. The astringent additive may be present in the shaving composition in an amount of from about 0.1 to about 35% by weight, preferably from about 1 to about 20% by weight, and most preferably from about 2 to about 10% by weight, all weights being based on the weight of the composition.

According to another aspect of the present invention, there is provided a process for inhibiting the re-entrant penetration of newly shaved hair into human skin. The process involves contacting the area to be shaved, prior to shaving, with the above-described shaving composition.

The present invention will be better understood by the following examples, all of which are intended to be illustrative only, and are not meant to unduly limit the scope of the invention.

EXAMPLES

Example 1

A non-foaming shaving gel was prepared per the following formulation.

| Component | % by weight |
|---|---|
| water | 91.04 |
| ELESTAB ® 338 | 2.50 |
| hydroxyethyl cellulose | 0.50 |
| CARBOMER ® | 0.16 |
| sodium hydroxide (1N) | 0.80 |
| LARICYL ® LS 8865 | 5.00 |

The non-foaming shaving gel was applied onto human skin, prior to shaving, producing a strong tingling/tightening sensation during the contact time required for shaving.

Example 2

A foaming shave gel was prepared per the following formulation.

| Component | % by weight |
|---|---|
| water | 37.10 |
| ELESTAB ® 338 | 1.00 |
| hydroxypropyl methylcellulose | 0.60 |
| triethanolamine (99%) | 0.30 |
| cocamide MEA | 5.50 |
| citric acid (50%) | 0.30 |
| ammonium lauryl sulfate | 28.00 |
| ammonium laureth sulfate | 21.00 |
| dimethicone copolyol | 0.20 |
| lauryl glycoside | 2.00 |
| cocoglycoside + glycerol oleate | 1.00 |
| LARICYL ® LS 8865 | 3.00 |

Example 3

A foaming shave gel was prepared per the following formulation.

| Component | % by weight |
|---|---|
| water | 35.80 |
| ELESTAB ® 338 | 1.00 |
| hydroxypropyl methylcellulose | 0.50 |
| triethanolamine (99%) | 0.30 |
| cocamide MEA | 6.00 |
| ammonium lauryl sulfate | 28.00 |
| ammonium laureth sulfate | 23.00 |
| dimethicone copolyol | 0.20 |
| cocamidopropylamine oxide | 2.00 |
| LARICYL ® LS 8865 | 3.00 |

What is claimed is:

1. A shaving composition comprising a skin-tightening effective amount of an astringent additive containing a mixture of butylene glycol and mushroom extract.

2. The composition of claim 1 wherein the astringent additive is present in the composition in an amount of from about 0.1 to about 35% by weight, based on the weight of the composition.

3. The composition of claim 1 wherein the astringent additive is present in the composition in an amount of from about 1 to about 20% by weight, based on the weight of the composition.

4. The composition of claim 1 wherein the astringent additive is present in the composition in an amount of from about 2 to about 10% by weight, based on the weight of the composition.

5. A shaving gel comprising:

(a) an astringent compound containing a mixture of butylene glycol and mushroom extract;

(b) a water-soluble soap and/or synthetic wetting agent; and (c) water.

6. The gel of claim 5 wherein the astringent additive is present in the composition in an amount of from about 0.1 to about 35% by weight, based on the weight of the composition.

7. The gel of claim 5 wherein the astringent additive is present in the composition in an amount of from about 1 to about 20% by weight, based on the weight of the composition.

8. The gel of claim 5 wherein the astringent additive is present in the composition in an amount of from about 2 to about 10% by weight, based on the weight of the composition.

9. A process for inhibiting re-entrant penetration of newly shaved hair into human skin comprising:

(a) providing a shaving composition containing a skin-tightening effective amount of an astringent compound, the astringent compound containing a mixture of butylene glycol and mushroom extract; and (b) applying the shaving composition onto human skin prior to shaving.

10. The process of claim 2 wherein the astringent additive is present in the composition in an amount of from about 0.01 to about 35% by weight, based on the weight of the composition.

11. The process of claim 2 wherein the astringent additive is present in the composition in an amount of from about 1 to about 20% by weight, based on the weight of the composition.

12. The process of claim 2 wherein the astringent additive is present in the composition in an amount of from about 2 to about 10% by weight, based on the weight of the composition.

* * * * *